US011795222B2

(12) United States Patent
Boyer-Chammard et al.

(10) Patent No.: US 11,795,222 B2
(45) Date of Patent: Oct. 24, 2023

(54) TREATMENT OF HEAD AND NECK CANCER

(71) Applicant: INNATE PHARMA, Marseilles (FR)

(72) Inventors: Agnes Boyer-Chammard, Marseilles (FR); Pierre Dodion, Overijse (BE); Roger Cohen, Jenkintown, PA (US)

(73) Assignee: INNATE PHARMA, Marseilles (FR)

( * ) Notice: Subject to any disclaimer, the term of this patent is extended or adjusted under 35 U.S.C. 154(b) by 280 days.

(21) Appl. No.: 16/979,323

(22) PCT Filed: Mar. 12, 2019

(86) PCT No.: PCT/EP2019/056174
§ 371 (c)(1),
(2) Date: Sep. 9, 2020

(87) PCT Pub. No.: WO2019/175182
PCT Pub. Date: Sep. 19, 2019

(65) Prior Publication Data
US 2021/0061909 A1    Mar. 4, 2021

Related U.S. Application Data

(60) Provisional application No. 62/642,292, filed on Mar. 13, 2018.

(51) Int. Cl.
C07K 16/28      (2006.01)
A61P 35/00     (2006.01)
A61K 39/00     (2006.01)
C07K 16/30      (2006.01)

(52) U.S. Cl.
CPC .......... *C07K 16/2803* (2013.01); *A61P 35/00* (2018.01); *C07K 16/2863* (2013.01); *C07K 16/30* (2013.01); *A61K 2039/507* (2013.01); *A61K 2039/545* (2013.01); *C07K 2317/24* (2013.01); *C07K 2317/565* (2013.01); *C07K 2317/76* (2013.01)

(58) Field of Classification Search
CPC ....................... C07K 16/2803; C07K 16/2863; C07K 16/30; C07K 2317/24; C07K 2317/565; C07K 2317/76; A61P 35/00; A61K 2039/507; A61K 2039/545
See application file for complete search history.

(56) References Cited

U.S. PATENT DOCUMENTS

| 8,206,709 | B2 | 6/2012 | Spee et al. |
| 8,796,427 | B2 | 8/2014 | Spee et al. |
| 8,901,283 | B2 | 12/2014 | Spee et al. |
| 8,993,319 | B2 | 3/2015 | Moretta et al. |
| 9,422,368 | B2 | 8/2016 | Spee et al. |
| 9,512,228 | B2 | 12/2016 | Soederstroem et al. |
| 9,683,041 | B2 | 6/2017 | Spee et al. |
| 10,160,810 | B2 | 12/2018 | Moretta et al. |
| 10,329,348 | B2 | 6/2019 | Andre et al. |
| 10,676,523 | B2 | 6/2020 | Andre et al. |
| 10,709,782 | B2 | 7/2020 | Parshad |
| 10,711,063 | B2 | 7/2020 | Andre et al. |
| 10,870,700 | B2 | 12/2020 | Andre et al. |
| 11,225,519 | B2 | 1/2022 | Andre et al. |
| 11,572,410 | B2 | 2/2023 | Andre et al. |
| 2011/0229486 | A1 | 9/2011 | Moretta et al. |
| 2015/0132316 | A1* | 5/2015 | Moretta ................ A61P 9/00 435/7.24 |
| 2017/0073417 | A1 | 3/2017 | Soederstroem et al. |
| 2017/0253658 | A1 | 9/2017 | Van der Burg et al. |
| 2017/0281809 | A1 | 10/2017 | Spee et al. |
| 2019/0248896 | A1 | 8/2019 | Spee et al. |
| 2020/0109206 | A1 | 4/2020 | Soederstroem et al. |
| 2020/0299383 | A1 | 9/2020 | Andre et al. |
| 2021/0122821 | A1 | 4/2021 | Andre et al. |
| 2021/0238285 | A1 | 8/2021 | Andre et al. |
| 2021/0253694 | A1 | 8/2021 | Abdullah et al. |

FOREIGN PATENT DOCUMENTS

WO    2016/041947 A1    3/2016
WO    2016/062851 A1    4/2016

OTHER PUBLICATIONS

Balermpas et al (Combined Cetuximab and Reirradiation for Locoregional Recurrent and Inoperable Squamous Cell Carcinoma of the Head and Neck, Strahlentherapie und Onkologie, No. 12, 2009) (Year: 2009).*

Anonymous, "Archive History for NCT02643550 Study of Monalizumab and Cetuximab in Patients with Recurrent or Metastatic Squamous Cell Carcinoma of the Head and Neck," Nov. 24, 2016, Retrieved from the Internet: URL:https://clinicaltrials.gov/ct2/history/NCT02643550?V_3=View#StudyPageTop, Retrieved on May 5, 2019.

Cohen, R, et al., "Abstract 5666: Safety of the first-in-class anti-NKG2A monoclonal antibody Monalizumab in combination with cetuximab: a phase Ib/II study in recurrent or metastatic squamous cell carcinoma of the head and neck (R/M SCCHN)," Cancer Research, vol. 77, No. 13 Suppl. Jul. 1, 2017.

Innate Pharma, "R&D Update," Apr. 10, 2014, pp. 1-108, Retrieved from the Internet: URL:http://innate-pharma.com/sites/default/files/140410_rd?day_final_0.pdf, Retrieved on Dec. 1, 2015, pp. 70, 74.

(Continued)

*Primary Examiner* — Mark Halvorson
*Assistant Examiner* — Dennis J Sullivan
(74) *Attorney, Agent, or Firm* — SALIWANCHIK, LLOYD & EISENSCHENK

(57) ABSTRACT

This invention relates to the use of NKG2A-targeting agents for the treatment of cancers, notably head and neck cancers, in a patient having received prior treatment with cetuximab. This invention also provides advantageous combination regimens for use with NKG2A-targeting agents for the treatment of cancers.

14 Claims, No Drawings

Specification includes a Sequence Listing.

(56) References Cited

OTHER PUBLICATIONS

Levy, E.M., et al., "Cetuximab-mediated cellular cytotoxicity is inhibited by HLA-E membrane expression in colon cancer cells," Innate Immunity, vol. 15, No. 2, Apr. 1, 2009, pp. 91-100.

Ferris, R.L., et al., "Rationale for combination of therapeutic antibodies targeting tumor cells and immune checkpoint receptors: Harnessing innate and adaptive immunity through IgG1 isotype immune effector stimulation," Cancer Treatment Reviews, vol. 63, Dec. 2, 2017, pp. 48-60.

Cohen, R., et al.: "Abstract CT158: Phase II study of Monalizumab, a first-in-class NKG2A monoclonal antibody, in combination with cetuximab in previously treated recurrent or metastatic squamous cell carcinoma of the head and neck (R/M SCCHN): Preliminary assessment of safety and efficacy," Cancer Research, vol. 78, No. 13 Suppl., Jul. 18, 2018, pg. CT158.

Pascale, A., et al., "Anti-NKG2A mAB is a Checkpoint Inhibitor that Promotes Anti-Tumor Immunity by Unleashing Both T and NK Cells," Cell, vol. 175, No. 7, Dec. 13, 2018, p. 1731.

Claims as filed in U.S. Appl. No. 18/164,649, filed Feb. 6, 2023, p. 1.

Claims as filed in U.S. Appl. No. 17/768,484, filed Apr. 13, 2022, pp. 1-4.

Schilling, B. et al. "IRX-2, a novel immunotherapeutic, enhances and protects NK-cell functions in cancer patients" Cancer Immunol Immunother, 2012, pp. 1395-1405, vol. 61.

Vermorken, J. B. et al. "Cisplatin, Fluorouracil, and Docetaxel in Unresectable Head and Neck Cancer" The New England Journal of Medicine, Oct. 25, 2007, pp. 1695-1704, vol. 357.

Therapeutic Antibody Engineering, Chapter 10, "Antibody Fc engineering for optimal antibody performance", eds. Willaim R. Strohl, Lila M. Strohl, Woodhead Publishing, 2012, pp. 225-249 and pp. 459-595.

* cited by examiner

SEQUENCE LISTING

```
<160> NUMBER OF SEQ ID NOS: 17

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220
```

```
Ile Ile Tyr His Cys Lys His Lys Leu
225                 230
```

<210> SEQ ID NO 2
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335
```

-continued

```
Ile Glu Lys Thr Ile Ser Lys Ala Lys Gly Gln Pro Arg Glu Pro Gln
                340                 345                 350

Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 3
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
```

```
                225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
        450

<210> SEQ ID NO 4
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125
```

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 5
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Gln Ser Gly Ala Glu Val Lys Lys Pro Gly Ala
1               5                   10                  15

-continued

Thr Val Lys Ile Ser Cys Lys Val Ser Gly Tyr Thr Phe Ser Tyr
                20                  25                  30

Trp Met Asn Trp Val Gln Gln Ala Pro Gly Lys Gly Leu Glu Trp Met
            35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu

```
              435                 440                 445

Ser Leu Gly Lys
    450

<210> SEQ ID NO 6
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Gln Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 7
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Ser Tyr Trp Met Asn
1               5

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Arg Ile Asp Pro Tyr Asp Ser Glu Thr His Tyr
1               5                   10

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Arg Ile Asp Pro Tyr Asp Ser Glu Thr His Tyr Ser Pro Ser Phe Gln
1               5                   10                  15

Gly

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Arg Ile Asp Pro Tyr Asp Ser Glu Thr His Tyr Ala Gln Lys Leu Gln
1               5                   10                  15

Gly

<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 12

Gly Gly Tyr Asp Phe Asp Val Gly Thr Leu Tyr Trp Phe Phe Asp Val
1               5                   10                  15

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Ala Ser Glu Asn Ile Tyr Ser Tyr Leu Ala
1               5                   10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asn Ala Lys Thr Leu Ala Glu
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gln His His Tyr Gly Thr Pro Arg Thr
1               5

<210> SEQ ID NO 16
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser

```
<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg
                100                 105
```

TREATMENT OF HEAD AND NECK CANCER

CROSS-REFERENCE TO RELATED APPLICATIONS

This application is a U.S. National Stage application of International Application No. PCT/EP2019/056174, filed on Mar. 12, 2019, said International Application No. PCT/EP2019/056174 claims benefit under 35 U.S.C. § 119(e) of the U.S. Provisional Application No. 62/642,292, filed Mar. 13, 2018. Each of the above listed applications is incorporated by reference herein in its entirety for all purposes.

REFERENCE TO THE SEQUENCE LISTING

This application incorporates by reference a Sequence Listing submitted with this application as text file entitled NKG2A-109-WO-PCT_SL.TXT, created on Jul. 24, 2020, and having a size of 28,860 kilobytes.

FIELD OF THE INVENTION

This invention relates to the use of NKG2A-targeting agents for the treatment of cancers, notably head and neck cancers. This invention also provides advantageous combination regimens for use with NKG2A-targeting agents for the treatment of cancers.

BACKGROUND OF THE INVENTION

Natural Killer (NK) cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46 (see, e.g., Lanier (2001) Nat Immunol 2:23-27). Another important activating receptor involved in target cell lysis by NK cells is NKG2D. NKG2D recognizes the major histocompatibility complex (MHC) class I-related antigens of the MICA/B and ULBP protein families; the latter are stress-related proteins that are capable of acting as tumor-specific antigens permitting NK cells to recognize and eliminate tumor cells.

CD94/NKG2A is an inhibitory receptor found on subsets of natural killer cells (NK cells), Natural Killer T cells (NKT cells) and T cells ($\alpha/\beta$ and $\gamma/\delta$). CD94/NKG2A restricts cytokine release and cytotoxic responses of aforementioned lymphocytes towards cells expressing the CD94/NKG2A-ligand HLA-E (see, e.g., WO99/28748). HLA-E has also been found to be secreted in soluble form by certain tumor cells (Derre et al., J Immunol 2006; 177:3100-7) and activated endothelial cells (Coupel et al., Blood 2007; 109: 2806-14). Antibodies that inhibit CD94/NKG2A signalling may increase the cytokine release and cytolytic activity of lymphocytes towards HLA-E positive target cells, such as responses of CD94/NKG2A-positive NK cells responses towards virally infected cells. Therefore, therapeutic antibodies that inhibit CD94/NKG2A but that do not provoke the killing of CD94/NKG2A-expressing cells (i.e. non-depleting antibodies), may induce control of tumor-growth in cancer patients.

Various antibodies against NKG2A have been described in the art. WO2008/009545 describes humanized anti-NKG2A antibody Z270 while WO2009/092805 describes humanized anti-NKG2A antibody Z199. Vance et al. (J Exp Med 1999; 190: 1801-12) refers to rat anti-murine NKG2-antibody 20D5 (now commercially available via BD Biosciences Pharmingen, Catalog No. 550518, USA); and U.S. patent application publication 20030095965 describes murine antibody 3S9, which purportedly binds to NKG2A, NKG2C and NKG2E.

Head and neck squamous cell carcinoma (HNSCC) has an incidence of about 600,000 cases per year and mortality rate of about 50%. The major risk factors for HNSCC are tobacco use, alcohol consumption, and infection with human papilloma virus (HPV). Despite advances in knowledge of its epidemiology and pathogenesis, the survival rates for many types of HNSCC have improved little over the past forty years. The overall 5-year survival rate of HNSCC patients is only about 50%. Tobacco, alcohol consumption and viral agents are the major risk factors for development of HNSCC. These risk factors, together with genetic susceptibility, result in the accumulation of multiple genetic and epigenetic alterations in a multistep process of cancer development, and the understanding of such molecular carcinogenesis of HNSCC is being used for the development of targeted agents for treating HNSCC.

The idea of immunotherapy as a treatment for HNSCC has been in existence for decades, and attempts at treating HNSCC have involved targeting of tumor-specific antigens. Although improvements have been made in using such immune stimulatory treatment strategies for a variety of solid cancers, the use of these strategies for patients with head and neck squamous cell carcinoma (HNSCC) is lagging behind. Immunotherapeutic approaches for HNSCC are particularly complicated by the profound immune suppression that is induced by HNSCC, which potentially decreases the effectiveness of immune stimulatory efforts. A review of mechanisms by which HNSCC escapes the anti-tumor immune response, such as down-modulation of HLA class I, is provided in Duray et al. (2010) Clin. Dev. Immunol. Article ID 701657; 2010: 1-15.

Standard of care for HNSCC includes cisplatin-based chemotherapies, including combinations with cetuximab for the treatment of metastatic HNSCC. For the treatment of unresectable non-metastatic HNSCC, treatments include cisplatin-based chemotherapies as well as the combination of cetuximab and radiotherapy. The c225 antibody (cetuximab, ERBITUX®) is an anti-EGFR antibody demonstrated to inhibit EGF-mediated tumor cell growth in vitro which has been approved by the FDA for treatment of head and neck cancer in 2011. Cetuximab is thought to act through blocking oncogenic signaling of the EGF receptor pathway and by inducing Fcγ receptor-mediated antibody dependent cellular cytotoxicity (ADCC). In HNSCC however, ADCC may be affected by the profound immune suppression that is induced. At the same time, Vantourout et al., Sci. Transl. Med. 6: 231ra49 (2014) report that blocking oncogenic signaling of the EGF receptor pathway results in posttranscriptional regulation in tumor cells of major histocompatibility complex (MHC) class I-related antigens of the MICA/B and ULBP protein families which are recognized by the activating receptor NKG2D on NK cells and subsets of T cells. In particular, the expression by tumor cells of these stress-related antigens which are the natural ligands of NKG2D is decreased by clinical EGFR inhibitors, thus potentially decreasing the tumor cells' visibility to NK and T cells.

However, since many HNSCC patients receiving different treatments progress despite currently approved therapies, there is a need in the art to identify patient populations who could benefit most from treatments with immunotherapeutic agents.

SUMMARY OF THE INVENTION

The present invention arises, inter alia, from the observation that blockade of inhibitory receptor NKG2A using an anti-NKG2A antibody in combination with cetuximab provides clinical responses in patients having cancer, in particular head and neck cancer and notably HNSCC, including in patients having received prior platinum-based therapy and whose cancer has progressed (e.g. not responded, relapsed or otherwise progressed). Furthermore, the combination of anti-NKG2A antibody in combination with cetuximab gave rise to clinical responses even in patients whose cancer had progressed during or following prior treatment with cetuximab. In some embodiments, the patient may have been treated with prior cetuximab and/or a chemotherapeutic agent (e.g. platinum based therapy) or cetuximab and radiotherapy. In one embodiment, the combination therapies disclosed herein can be particularly advantageous for use in treating the patient population that has incurable unresectable and/or metastatic HNSCC, optionally further wherein the patient has received prior platinum-based therapy, radiotherapy and/or cetuximab.

Accordingly, in one aspect, neutralizing anti-NKG2A antibody in combination with cetuximab may provide significant amelioration of a cancer in the population of individuals having unresectable (e.g. incurable unresectable) and/or metastatic) head and neck cancer, notably HNSCC, which cancer has been deemed resistant to cetuximab. This combination treatment may provide an opportunity for a significant population of individuals with head and neck cancer, notably HNSCC whose cancer progresses despite treatment with cetuximab. In particular, the combination treatment may be valuable in preventing further progression, notably to delay or prevent metastatic cancer (e.g. in individuals having non-metastatic cancer).

Provided herein are methods for treating a head and neck cancer in an individual having a head and neck cancer. In one embodiment, the cancer in unresectable (head and neck cancer that cannot be completely removed through surgery). In one embodiment, provided is a method for decreasing tumor burden (e.g. decrease in the sum of diameters of target cell lesions compared to baseline sum of diameters) in an individual having an unresectable and/or metastatic head and neck cancer.

In one embodiment, the method comprises treating a head and neck cancer in an individual, the method comprising administering to the individual a therapeutically active amount of an agent that neutralizes the inhibitory activity of a human NKG2A polypeptide, in combination with cetuximab. In one embodiment, the individual has cancer that has progressed during or following a prior course of treatment with cetuximab (the prior course of treatment with cetuximab does not include a compound that neutralizes the activity of NKG2A, but it may be administered in combination with other treatments, notably radiotherapy and/or chemotherapy). In one embodiment, in addition to a prior course of therapy with cetuximab (optionally combined with a chemotherapeutic agent or radiotherapy), the individual has received a further prior course of therapy with a chemotherapeutic agent; for example, the individual received a first prior course of therapy with a platinum-based agent, followed by a second prior course of therapy with cetuximab. In one embodiment, the cancer is an unresectable (e.g. incurable unresectable) and/or metastatic head and neck cancer.

In one embodiment, provided is a method for treating a head and neck cancer in an individual having an unresectable, optionally non-metastatic, head and neck cancer, notably HNSCC, the method comprising administering to the individual: (a) a therapeutically active amount of an agent that neutralizes the activity of a human NKG2A polypeptide, (b) a therapeutically active amount of cetuximab. In one embodiment, the individual has received a prior treatment with a chemotherapeutic agent (e.g. a platinum-based therapy), radiotherapy and/or cetuximab (e.g. a prior course of treatment that comprises administration of such chemotherapeutic agent, radiotherapy and/or cetuximab) and whose head and neck cancer has progressed during or following such prior treatment. In one embodiment, the individual has a head and neck cancer that did not respond to or not sufficiently responded to treatment with such chemotherapeutic agent, radiotherapy and/or cetuximab. In one embodiment, the individual has a head and neck cancer that relapsed following treatment with such chemotherapeutic agent, radiotherapy and/or cetuximab. In one example, an individual has received a prior course of treatment that comprised administration of chemotherapeutic agent (e.g. platinum-based therapy), radiotherapy and/or cetuximab and has experienced cancer progression or relapse following the completion of the course of treatment, e.g. within 3 years or less of completion of the course of treatment. In one embodiment, the individual has received cetuximab combined with radiation therapy. In one embodiment, the individual has received platinum-based therapy followed by or combined with cetuximab therapy. In another embodiment, the individual has received prior treatment with cetuximab.

In one embodiment, provided is a method for treating a head and neck cancer in an individual having a head and neck cancer who has received a prior treatment with cetuximab (e.g. a prior course of treatment that comprises administration of cetuximab) and whose cancer has progressed, the method comprising administering to the individual: (a) a therapeutically active amount of an agent that neutralizes the activity of a human NKG2A polypeptide, (b) a therapeutically active amount of cetuximab. In one example, an individual having a head and neck cancer has received a prior course of treatment that comprised administration of cetuximab and has not, or has not sufficiently, responded to such treatment. In one example, an individual has received a prior course of treatment that comprised administration of cetuximab and has experienced cancer progression or relapse during or after said course of treatment that comprised cetuximab. In one example, an individual has received a prior course of treatment that comprised administration of cetuximab and has experienced cancer progression or relapse following the completion of said prior course of treatment that comprised cetuximab, e.g. within 3 years of completion of said prior course of treatment. The prior course of treatment that comprised cetuximab may for example have comprised cetuximab combined with radiation therapy. In one embodiment, the prior course of treatment that comprised cetuximab comprised cetuximab combined with radiation and/or a chemotherapeutic agent, e.g. a platinum-based agent.

In one embodiment, provided is a method for treating or preventing progression of HNSCC in an individual comprising: (i) identifying an individual who has HNSCC that is resistant to treatment with cetuximab (e.g. has progressed despite treatment with cetuximab, optionally cetuximab combined with radiotherapy and/or chemotherapy), and (ii) administering to the individual an effective amount of agent that neutralizes the inhibitory receptor NKG2A in combination with cetuximab. In one embodiment, the individual of step (i) has unresectable, non-metastatic head and neck cancer. In one embodiment, the individual of step (i) has unresectable and metastatic head and neck cancer.

In another embodiment, provided is a method for determining whether an individual (or, e.g., a population of individuals) having an HNSCC, optionally an unresectable head and neck cancer, optionally non-metastatic head and neck cancer, optionally metastatic head and neck cancer, may derive particular benefit from, be responsive to and/or suitable for treatment with an agent that neutralizes the inhibitory receptor NKG2A in combination with cetuximab, the method comprising determining whether the individual (s) has a head and neck cancer that is resistant to cetuximab (e.g. cetuximab as monotherapy, cetuximab in combination with radiotherapy, and/or cetuximab in combination with chemotherapy), wherein a determination that the individual (s) has a head and neck cancer that is resistant to cetuximab indicates that the individual(s) may derive particular benefit from, be responsive to and/or suitable for treatment with an agent that neutralizes the inhibitory receptor NKG2A in combination with cetuximab. Optionally, the method further comprises a step of administering an agent that neutralizes the inhibitory receptor NKG2A in combination with cetuximab to the individual who is determined to derive particular benefit from, be responsive to and/or suitable for such treatment.

Also provided herein are compositions for use in the treatment of disease, e.g. cetuximab resistant cancer. In some embodiment, provided is an agent that neutralizes the inhibitory activity of human NKG2A and/or cetuximab, for use in the treatment of a HNSCC in an individual whose HNSCC cancer is resistant to treatment (e.g. prior treatment) with cetuximab (e.g. cetuximab alone or in combination with another agent such as chemotherapy or radiation therapy). In one embodiment, provided is an agent that neutralizes the inhibitory activity of human NKG2A, for use in the treatment of a cancer in an individual having received prior treatment with cetuximab. In one embodiment, the agent that neutralizes the inhibitory activity of human NKG2A is administered in combination with cetuximab. In one embodiment, provided is an agent that neutralizes the inhibitory activity of human NKG2A for use in treating a HNSCC in a human individual having received prior treatment with cetuximab, the treatment comprising administering to the individual an effective amount of each of: (a) an agent, optionally an antibody, that neutralizes the inhibitory activity of human NKG2A, and (b) cetuximab. In one embodiment, the cancer or carcinoma is HNSCC. In one embodiment, provided is an agent that neutralizes the inhibitory activity of human NKG2A for use in treating a cancer in a human individual having an unresectable, optionally non-metastatic, carcinoma, the treatment comprising administering to the individual an effective amount of each of: (a) an agent, optionally an antibody, that neutralizes the inhibitory activity of human NKG2A, and (b) cetuximab. In one embodiment, the cancer or carcinoma is HNSCC. In one embodiment, provided is cetuximab, for use in the treatment of a HNSCC in an individual having received a prior treatment (e.g. a first course of treatment with cetuximab), wherein said treatment comprises administering to the individual an effective amount of each of: (a) an agent, optionally an antibody, that neutralizes the inhibitory activity of human NKG2A, and (b) cetuximab (e.g. a second course of treatment with cetuximab).

In any embodiment herein, the individual is characterized as having a HNSCC cancer that has progressed despite treatment with cetuximab. Optionally, the individual has a HNSCC cancer that has progressed despite prior treatment with cetuximab combined with radiotherapy.

In any embodiment herein, a head and neck cancer that is resistant to treatment with cetuximab is a cancer that has progressed or relapsed during or following a prior course of treatment that comprised cetuximab. In one example, a cancer that is resistant to treatment with cetuximab is a cancer that has progressed or relapsed following the completion of a prior course of treatment that comprised cetuximab, e.g. within 3 years or less. For example a cancer may have progressed within 2 years, or within 12 months, 6 months, 4 months, or 3 months of completion of the prior course of treatment comprising cetuximab. Optionally, the cancer that has relapsed is a cancer that is not a new primary cancer but represents a recurrence of the original HNSCC. Optionally, the cancer that has relapsed is a cancer that is of the same region and/or laterality (e.g. right or left side). The prior course of treatment that comprised cetuximab may for example have comprised cetuximab combined with radiation therapy. The prior course of treatment that comprised cetuximab may for example have comprised cetuximab combined with chemotherapy, such as platinum based therapy.

In one aspect of any of the embodiments herein, the treatment of the invention causes a decrease in tumor burden, optionally a decrease in the sum of diameters of target cell lesions compared to baseline sum of diameters. In one embodiment, the treatment delays the progression of cancer. In one embodiment, the treatment delays or prevents cancer metastasis. In one embodiment, the treatment by shrinking the growth of or delaying the growth of the cancer improves the patient's symptoms or well-being.

In any embodiment herein, the individual can be characterized as having received prior platinum-based therapy (and may possibly have a cancer that progressed despite such therapy). Platinum-based therapy can include, for example, administration of a treatment regimen comprising cisplatin or carboplatin, for example in a regimen comprising the platinum agent, and further paclitaxel, docetaxel, gemcitabine or 5FU (5-Fluorouracil).

In one embodiment, provided is a method for treating a HNSCC in an individual comprising:
  (a) administering to the individual cetuximab (e.g. administering a cycle or course of therapy comprising cetuximab, optionally a course of therapy comprising cetuximab and radiotherapy or comprising cetuximab and chemotherapy); and
  (b) if the cancer in the individual in step (a) is resistant to cetuximab (e.g. to the course of therapy of step (a)), optionally wherein the patient has cancer that is progressing, spreading to other organs or non-responsive), administering to the individual a therapeutically active amount of an agent that neutralizes the activity of a human NKG2A polypeptide in combination with a therapeutically active amount cetuximab.

In one embodiment, the individual has a non-metastatic HNSCC.

In one embodiment, the individual has received prior platinum-based therapy (e.g. and progressed despite such therapy).

In one embodiment, the cetuximab treatment of step (a) comprises combined treatment with radiotherapy and/or chemotherapy.

In one embodiment of any aspect herein, the agent that neutralizes the inhibitory activity of a human NKG2A polypeptide is an antibody capable of binding NKG2A. In one aspect, the agent that neutralizes the inhibitory activity of a human NKG2A polypeptide is a non-depleting antibody (e.g. an antibody that lacks an Fc domain or that has an Fc domain with minimal or no binding to one or more Fcγ receptors).

In one embodiment, the cancer is an oropharyngeal tumor, a larynx tumor, a tumor of the oral cavity, a tumor of the nasopharynx, or a tumor of the hypopharynx. In one embodiment, the HNSCC is an oral cavity SCC (OCSCC). OCSCC comprises squamous cell carcinoma of the lip, anterior ⅔ of the tongue, floor of the mouth, buccal mucosa, gingiva, hard palate and retromolar trigone.

In one embodiment the HNSCC is a non-metastatic cancer.

In one embodiment, the individual is human papillomavirus (HPV)-positive (e.g. characterized by the presence of human papillomavirus, positive for a HPV genotype associated with high cancer risk, positive for HPV16 genotype and/or positive for $P16^{INKa}$ expression).

In one embodiment, the individual is human papillomavirus (HPV)-negative (e.g. characterized by the absence of human papillomavirus, absence of a HPV genotype associated with high cancer risk, negative for HPV16 genotype and/or negative for $P16^{INKa}$ expression).

In one embodiment, the individual has a head and neck cancer characterized by the presence of lymphocytes in the tumor environment (e.g. within tumor tissue and/or within tumor adjacent tissue).

In one embodiment, the anti-NKG2A antibody is administered in an amount that results in the neutralization of the inhibitory activity of human CD94/NKG2A in the human patient (in vivo), optionally wherein the anti-NKG2A antibody is administered at a dose that results in saturation of NKG2A polypeptides on peripheral blood NK and T lymphocyte for at least two weeks, optionally at least four weeks. In one embodiment, the anti-NKG2A antibody is administered at a dose of between 1 mg/kg and 10 mg/kg, optionally at about 4 mg/kg, optionally at about 10 mg/kg. In one embodiment, the anti-NKG2A antibody is administered at a fixed dose in the range of 100-1000 mg, optionally in the range of 200-1200 mg, for example 750 mg.

Optionally, HLA-E status of a cancer can be assessed prior to treatment with an anti-NKGA agent. In one embodiment provided is a method combining a HLA-E detection step to identify patients having HLA-E+ HNSCC; these patients can thereafter be treated with an agent that neutralizes the inhibitory activity of a NKG2A polypeptide.

In one embodiment, the agent that neutralizes the activity of a human NKG2A polypeptide is an anti-NKG2A antibody that is administered in an effective amount that results in the neutralization of the inhibitory activity of human CD94/NKG2A in the human patient (in vivo), optionally wherein the anti-NKG2A antibody is administered at a dose that results in neutralization of NKG2A in peripheral blood NK and T lymphocyte for at least two weeks, optionally at least four weeks. In one aspect, the combination is administered (or is for administration) according to a particular clinical dosage regimen, notably at a particular dose amount and according to a specific dosing schedule (e.g. dose amount and/or according to a specific dosing schedule provided herein).

In one embodiment, the agent that neutralizes the activity of a human NKG2A polypeptide is an antibody that reduces the inhibitory activity of NKG2A by blocking binding of its ligand, HLA-E, i.e., the anti-NKG2A antibody interferes with the binding of NKG2A by HLA-E. The antibody having the heavy chains of any one of SEQ ID NOS: 2-6 and a light chain of SEQ ID NO: 7 is an example of such an antibody. In one embodiment, the anti-NKG2A antibody reduces the inhibitory activity of NKG2A without blocking binding of its ligand, HLA-E, i.e., the anti-NKG2A agent is a non-competitive antagonist and does not interfere with the binding of NKG2A by HLA-E. The antibody having the heavy and light chain variable regions of SEQ ID NOS: 16 and 17 respectively is an example of such an antibody.

In one embodiment, the anti-NKG2A agent is an antibody which binds with a significantly higher affinity to NKG2A than to one or more activating NKG2 receptors. For example, in one embodiment, the agent is an antibody which binds with a significantly higher affinity to NKG2A than to NKG2C. In an additional or alternative embodiment, the agent is an antibody which binds with a significantly higher affinity to NKG2A than to NKG2E. In an additional or alternative embodiment, the agent is an antibody which binds with a significantly higher affinity to NKG2A than to NKG2H. The antibody having the heavy chains of any one of SEQ ID NOS: 2-6 and light chain of SEQ ID NO: 7, respectively, binds NKG2A without substantially binding to NKG2C, NKG2E or NKG2H.

In an additional or alternative embodiment, the anti-NKG2A agent competes with the antibody having the heavy chains of any one of SEQ ID NOS: 2-6 and light chain of SEQ ID NO: 7, and/or the antibody having the heavy and light chain variable regions of SEQ ID NOS: 16 and 17 respectively, in binding to CD94/NKG2A. The agent can be, e.g., a human or humanized anti-NKG2A antibody.

In one embodiment, the anti-NKG2A antibody is a humanized antibody having the heavy chains of any one of SEQ ID NOS: 2-6 and light chain of SEQ ID NO: 7. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided.

In other embodiments, pharmaceutical compositions and kits are provided, as well as methods for using them.

These aspects are more fully described in, and additional aspects, features, and advantages will be apparent from, the description of the invention provided herein.

Definitions

Where "comprising" is used, this can optionally be replaced by "consisting essentially of" or by "consisting of".

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence: MDNQGVIYSDLNLPPNPKRQQRKPKGNKSSILATE-QEITYAELNLQKASQDFQGNDKTYHC KDLPSA-PEKLIVGILGIICLILMASVVTIVVIP-STLIQRHNNSSLNTRTQKARHCGHCPEEWITY SNSCYYIGKERRTWEESLLACTSKNSSLLSID-NEEEMKFLSIISPSSWIGVFRNSSHHPWVT MNGLAFKHEIKDSDNAELN-CAVLQVNRLKSAQCGSSIIYHCKHKL (SEQ ID NO:1).

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g., such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

In the context of the present disclosure, "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "CD94/NKG2A positive lymphocyte" also includes immortal cell lines of lymphoid origin (e.g. NKL, NK-92).

In the context of the present disclosure, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, preferably at least a 40% or 50% augmentation in lymphocyte cytotoxicity, or more preferably at least a 70% augmentation in NK cytotoxicity", and referring to the cytotoxicity assays described. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E* LCL 721.221-Cw3 cells due to HLA-E-induced inhibitory signaling via CD94/NKG2A. When NK cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 μg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn., IFN-γ: OptEIA set, Pharmingen).

Whenever within this whole specification "treatment of HNSCC" or the like is mentioned with reference to a NKG2A-neutralizing agent (e.g. antibody), there is meant: (a) method of treatment of HNSCC, said method comprising the step of administering (for at least one treatment) a NKG2A-neutralizing agent, (preferably in a pharmaceutically acceptable carrier material) to an individual, a mammal, especially a human, in need of such treatment, in a dose that allows for the treatment of HNSCC, (a therapeutically effective amount), preferably in a dose (amount) as specified herein; (b) the use of a NKG2A-neutralizing agent for the treatment of HNSCC, or a NKG2A-neutralizing agent, for use in said treatment (especially in a human); (c) the use of a NKG2A-neutralizing agent for the manufacture of a pharmaceutical preparation for the treatment of HNSCC, (d) a method of using a NKG2A-neutralizing agent for the manufacture of a pharmaceutical preparation for the treatment of HNSCC, comprising admixing a NKG2A-neutralizing agent with a pharmaceutically acceptable carrier, or a pharmaceutical preparation comprising an effective dose of a NKG2A-neutralizing agent that is appropriate for the treatment of HNSCC; or (e) any combination of (a), (b), (c) and (d), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of antibodies.

The term "specifically binds to" means that an antibody can bind preferably in a competitive binding assay to the binding partner, e.g. NKG2A, as assessed using either recombinant forms of the proteins, epitopes therein, or native proteins present on the surface of isolated target cells. Competitive binding assays and other methods for determining specific binding are well known in the art. For example binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target. An agent that specifically binds NKG2A may bind NKG2A alone or NKG2A as a dimer with CD94.

When an antibody is said to "compete with" a particular monoclonal antibody, it means that the antibody competes with the monoclonal antibody in a binding assay using either recombinant molecules (e.g., NKG2A) or surface expressed molecules (e.g., NKG2A). For example, if a test antibody reduces the binding of an antibody having a heavy chain of any of SEQ ID NO: 2 and a light chain of SEQ ID NO: 7 to a NKG2A polypeptide or NKG2A-expressing cell in a binding assay, the antibody is said to "compete" respectively with such antibody.

The term "affinity", as used herein, means the strength of the binding of an antibody to an epitope. The affinity of an antibody is given by the dissociation constant Kd, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of NKG2A-Neutralizing Agents

An agent that neutralizes the inhibitory receptor NKG2A can for example comprise an agent (e.g. a protein) that binds an extra-cellular portion of human CD94/NKG2A receptor or its natural ligand HLA-E, and reduces the inhibitory activity of human CD94/NKG2A receptor expressed on the surface of a CD94/NKG2A positive lymphocyte. In one embodiment the agent competes with HLA-E in binding to CD94/NKG2A, i.e. the agent blocks the interaction between CD94/NKG2A and its ligand HLA-E. In one embodiment the agent (e.g. an antibody) binds to CD94/NKG2A and blocks the interaction between CD94/NKG2A and its ligand HLA-E. In another embodiment, the agent that neutralizes the inhibitory receptor NKG2A is a protein (e.g. an antibody) that binds the human HLA-E polypeptide and inhibits the interaction between a human HLA-E protein and a human CD94/NKG2A protein. In another embodiment the agent does not compete with HLA-E in binding to CD94/NKG2A; i.e. the agent binds NKG2A and is capable of binding CD94/NKG2A simultaneously with HLA-E. The antibody may bind a combined epitope on CD94 and NKG2A or and epitope on NKG2A alone. In one embodiment, the antibody binds an epitope on NKG2A which at least partly overlaps with the HLA-E binding site.

In one aspect the anti-NKG2A agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR; and a multispecific antibody.

In one embodiment, the anti-NKG2A antibodies do not demonstrate substantial specific binding to Fcγ receptors, e.g., one or more (or all of) human CD16, CD32a, CD32b and CD64. Such antibodies may comprise constant regions of various heavy chains that are known not to bind Fc receptors. One such example is an IgG4 constant region. IgG4 Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The present disclosure thus concerns antibodies or other agents binding to NKG2A. In one aspect, the antibody binds to NKG2A with a KD at least 100-fold lower than to human NKG2C and/or NKG2E.

In one aspect of the disclosure, the agent reduces CD94/NKG2A-mediated inhibition of a CD94/NKG2A-expressing lymphocyte by interfering with CD94/NKG2A signalling by, e.g., interfering with the binding of HLA-E by NKG2A, preventing or inducing conformational changes in the CD94/NKG2A receptor, and/or affecting dimerization and/or clustering of the CD94/NKG2A receptor.

In one aspect of the disclosure, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10,000 fold lower than to NKG2C. In another aspect of the disclosure, the agent binds to an extracellular portion of NKG2A with a KD at least 100 fold lower than to NKG2C, NKG2E and/or NKG2H molecules. In a further preferred aspect, the agent binds to an extracellular portion of NKG2A with a KD at least 150, 200, 300, 400, or 10,000 fold lower than to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporate herein by reference.

The antibody can for example have an $EC_{50}$ for binding (high affinity) to NKG2A-expressing cells of between 0.5-10 ng/ml, optionally 1-5 ng/ml, optionally 1-10 ng/ml, optionally 1-20 ng/ml, e.g. about 4 ng/ml. The NKG2A-expressing cells can be, for example, NKG2A-expressing cells in human PBMC. In one embodiment, the NKG2A-expressing cells are cells made to express CD94/NKG2A, for example Ba/F3 cells stably overexpressing CD94/NKG2A as shown in Example 13 of U.S. Pat. No. 8,206,709, the disclosure of which is incorporated by reference. In one embodiment, the antibody has binding affinity ($K_D$), optionally wherein binding affinity is bivalent, for a human NKG2A polypeptide of less than $10^{-9}$ M, optionally less than $10^{-10}$ M, or optionally less than $10^{-11}$ M, optionally between than $10^{-10}$ M and $10^{-12}$ M, optionally between than $10^{-10}$ M and $10^{-11}$ M. Affinity can be assessed, for example, for binding to a single-chain NKG2A-CD94-mFc construct as described in U.S. Pat. No. 7,932,055, the disclosure of which is incorporated by reference).

The anti-NKG2A antibody can be a human or humanized antibody, for example comprising the respective VH and VL regions of the antibodies shown in the Table below.

| Antibody | VH | VL |
| --- | --- | --- |
| VH6 | SEQ ID NO: 2 | SEQ ID NO: 7 |
| VH1 | SEQ ID NO: 3 | SEQ ID NO: 7 |
| VH5 | SEQ ID NO: 4 | SEQ ID NO: 7 |
| VH7 | SEQ ID NO: 5 | SEQ ID NO: 7 |
| VH8 | SEQ ID NO: 6 | SEQ ID NO: 7 |
| Z199 | SEQ ID NO: 16 | SEQ ID NO: 17 |

The anti-NKG2A antibody can be a human or humanized antibody, for example comprising a VH human acceptor framework from a human acceptor sequence selected from, e.g., VH1_18, VH5_a, VH5_51, VH1_f, and VH1_46, and a JH6 J-segment, or other human germline VH framework sequences known in the art. The VL region human acceptor sequence may be, e.g., VKI_O2/JK4.

In one embodiment, the antibody is a humanized antibody or antibody fragment based on antibody Z270. Different humanized Z270VH chains are shown in SEQ ID NOS: 2-6 (variable region domain amino acids underlined). Humanized Z270VH light chain is shown in SEQ ID NO: 7. HumZ270 antibody is also disclosed in U.S. Pat. No. 8,206,709 (the disclosure of which is incorporated herein by reference). HumZ270VH6 (SEQ ID NO: 3) is based on VH5_51; HumZ270VH1 (SEQ ID NO: 2) is based on VH1_18; humZ270VH5 (SEQ ID NO: 4) is based on VH5_a; humZ270VH7 (SEQ ID NO: 5) is based on VH1_f; and humZ270VH8 (SEQ ID NO: 6) is based on VH1_46; all with a JH6 J-segment. Each of these antibodies retains high affinity binding to NKG2A, with low likelihood of a host immune response against the antibody as the 6 C-terminal amino acid residues of the Kabat CDR-H2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of any of SEQ ID NOS: 2-6, or an amino acid sequence at least 50%, 60%, 70%, 80%, 90%, 95%, 98% or 99% identical thereto, and (ii) a light chain variable region of SEQ ID NO: 7, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 2-6, or an amino acid sequence at least 50%, 60%, 70%, 80%, 90%, 95%, 98% or 99% identical thereto, and (ii) a light chain comprising the amino acid sequence of SEQ ID NO: 7, or an amino acid sequence at least 50%, 60%, 70%, 80%, 90%, 95%, 98% or 99% identical thereto. The antibody having the heavy chain comprising the sequence of any of SEQ ID NOS: 2-6 and a light chain comprising the sequence of SEQ ID NO: 7 neutralizes the inhibitory activity of NKG2A, but does not substantially bind the activating receptors NKG2C, NKGE or NKG2H. This antibody furthermore competes with HLA-E for binding to NKG2A on the surface of a cell. In one aspect, the agent comprises HCDR1, HCDR2 and/or HCDR3 sequences derived from the heavy chain having the amino acid sequence of any of SEQ ID NO: 2-6. In one aspect of the invention, the agent comprises LCDR1, LCDR2 and/or LCDR3 sequences derived from the light chain having the amino acid sequence of SEQ ID NO: 7.

```
Heavy Chains (variable region sunderlined)
VH1:
                                        (SEQ ID NO: 2)
QVQLVQSGAEVKKPGASVKVSCKASGYTFTSYWMNWVRQAPGQGLEWMGR

IDPYDSETHYAQKLQGRVTMTTDTSTSTAYMELRSLRSDDTAVYYCARGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
VH6:
                                        (SEQ ID NO: 3)
EVQLVQSGAEVKKPGESLKISCKGSGYSFTSYWMNWVRQMPGKGLEWMGR

IDPYDSETHYSPSFQGQVTISADKSISTAYLQWSSLKASDTAMYYCARGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
VH5:
                                        (SEQ ID NO: 4)
EVQLVQSGAEVKKPGESLRISCKGSGYSFTSYWMNWVRQMPGKGLEWMGR

IDPYDSETHYSPSFQGHVTISADKSISTAYLQWSSLKASDTAMYYCARGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
VH7:
                                        (SEQ ID NO: 5)
EVQLVQSGAEVKKPGATVKISCKVSGYTFTSYWMNWVQQAPGKGLEWMGR

IDPYDSETHYAEKFQGRVTITADTSTDTAYMELSSLRSEDTAVYYCATGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
VH8:
                                        (SEQ ID NO: 6)
QVQLVQSGAEVKKPGASVKVSCKASGYTFTSYWMNWVRQAPGQGLEWMGR

IDPYDSETHYAQKFQGRVTMTRDTSTSTVYMELSSLRSEDTAVYYCARGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
Light chain
                                        (SEQ ID NO: 7)
DIQMTQSPSSLSASVGDRVTITCRASENIYSYLAWYQQKPGKAPKLLIYN

AKTLAEGVPSRFSGSGSGTDFTLTISSLQPEDFATYYCQHHYGTPRTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In one aspect, the anti-NKG2A antibody is an antibody or antibody fragment comprising a CDR-H1 corresponding to residues 31-35 of any of SEQ ID NOS: 2-6 (the amino acid sequence SYWMN (SEQ ID NO: 8)), a CDR-H2 corresponding to residues 50-60 (the amino acid sequence RIDPYDSETHY (SEQ ID NO: 9)) (optionally 50-66 when including the 6 terminal amino acids of human origin, i.e. the sequence RIDPYDSETHYSPSFQG (SEQ ID NO: 10) for the VH6 heavy chain, the sequence RIDPYDSETHYAQKLQG (SEQ ID NO: 11) for the VH1 heavy chain, etc.) of any of SEQ ID NOS: 2-6, and a CDR-H3 corresponding to residues 99-114 (95-102 according to Kabat) of any of SEQ ID NOS: 2-6 (the amino acid sequence GGYDFDVGTLYWFFDV (SEQ ID NO: 12)). In one embodiment, the CDR-H2 corresponding to residues 50-66 of any of SEQ ID NOS: 2-6. Optionally, a CDR may comprise one, two, three, four, or more amino acid substitutions.

In one aspect, the anti-NKG2A antibody is an antibody or antibody fragment comprising a CDR-L1 corresponding to residues 24-34 of SEQ ID NO: 7 (the amino acid sequence RASENIYSYLA (SEQ ID NO: 13)), a CDR-L2 corresponding to residues 50-56 of SEQ ID NO: 7 (the amino acid sequence NAKTLAE (SEQ ID NO: 14)), and an CDR-L3 corresponding to residues 89-97 of SEQ ID NO: 7 (the amino acid sequence QHHYGTPRT (SEQ ID NO: 15)). Optionally, a CDR may comprise one, two, three, four, or more amino acid substitutions.

In one aspect, the anti-NKG2A antibody is an antibody or antibody fragment comprising a CDR-H1 corresponding to residues 31-35 of any of SEQ ID NOS: 2-6, a CDR-H2 corresponding to residues 50-60 (optionally 50-66) of any of SEQ ID NOS: 2-6, and a CDR-H3 corresponding to residues 99-114 (95-102 according to Kabat) of any of SEQ ID NOS: 2-6, a CDR-L1 corresponding to residues 24-34 of SEQ ID NO: 7, a CDR-L2 corresponding to residues 50-56 of SEQ ID NO: 7, and an CDR-L3 corresponding to residues 89-97 of SEQ ID NO: 7.

In one aspect, the agent is a fully human antibody which has been raised against the CD94/NKG2A epitope to which any of the aforementioned antibodies bind.

It will be appreciated that, while the aforementioned antibodies can be used, other antibodies can be prepared. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Most preferably, the epitope is the epitope specifically recognized by an antibody having the heavy chain of any of SEQ ID NOS: 2-6 and the light chain of SEQ ID NO: 7.

In one aspect, an anti-NKG2A antibody binds substantially the same epitope as an antibody having the heavy chain of any of SEQ ID NOS: 2-6 and the light chain of SEQ ID NO: 7, e.g. monalizumab. The antibody having the heavy chain of any of SEQ ID NOS: 2-6 and the light chain of SEQ ID NO: 7 has loss of binding to a NKG2A mutant having the following amino acid substitutions: K199A/D202A/V213S/R215A/K217A (reference to GenBank accession no. AAL65234.1). In one embodiment, an anti-NKG2A antibody used according to the disclosure binds to an epitope of NKG2A that at least partially overlaps with, or includes at least one residue in, the epitope bound by an antibody having the heavy chain of any of SEQ ID NOS: 2-6 and the light chain of SEQ ID NO: 7, e.g. monalizumab. The residues bound by the antibody can be specified as being present on the surface of the NKG2A polypeptide, e.g. in a NKG2A polypeptide expressed on the surface of a cell. The amino acid residues on NKG2A bound by the antibody can for example be selected from the group of residues consisting of K199, D202, V213, R215, and K217 (reference to GenBank accession no. AAL65234.1 or the NKG2A amino acid sequence of SEQ ID NO: 1).

Binding of an anti-NKG2A antibody to cells transfected with NKG2A mutants can be measured and compared to the ability of anti-NKG2A antibody to bind wild-type NKG2A polypeptide (SEQ ID NO: 1). A reduction in binding between an anti-NKG2A antibody and a mutant NKG2A polypeptide (e.g., a mutant NKG2A having the substitutions K199A/D202A/V213S/R215A/K217A) means that there is a reduction in binding affinity (e.g., as measured by known methods such FACS testing of cells expressing a particular mutant, or by Biacore testing of binding to mutant polypeptides) and/or a reduction in the total binding capacity of the anti-NKG2A antibody (e.g., as evidenced by a decrease in Bmax in a plot of anti-NKG2A antibody concentration versus polypeptide concentration). A significant reduction in binding indicates that the mutated residue is directly involved in binding to the anti-NKG2A antibody or is in close proximity to the binding protein when the anti-NKG2A antibody is bound to NKG2A.

In some embodiments, a significant reduction in binding means that the binding affinity and/or capacity between an anti-NKG2A antibody and a mutant NKG2A polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type NKG2A polypeptide. In certain embodiments, binding is reduced below detectable limits. In some embodiments, a significant reduction in binding is evidenced when binding of an anti-NKG2A antibody to a mutant NKG2A polypeptide is less than 50% (e.g., less than 45%, 40%, 35%, 30%, 25%, 20%, 15% or 10%) of the binding observed between the anti-NKG2A antibody and a wild-type NKG2A polypeptide.

In some embodiments, anti-NKG2A antibodies are provided that exhibit significantly lower binding for a mutant NKG2A polypeptide in which a residue in a segment comprising an amino acid residue bound by an antibody having the heavy chain of any of SEQ ID NOs: 2-6 and the light chain of SEQ ID NO: 7, e.g. monalizumab, is substituted with a different amino acid compared to binding to a wild-type NKG2A polypeptide (e.g. the polypeptide of SEQ ID NO: 1). In one embodiment, the mutant has the substitutions K199A, D202A, V213S. R215A and K217A by reference to wild-type NKG2A of SEQ ID NO: 1.

In one aspect, the agent comprises HCDR1, HCDR2 and/or HCDR3 sequences derived from the VH having the amino acid sequence of SEQ ID NO: 16. In one aspect of the disclosure, the agent comprises LCDR1, LCDR2 and/or LCDR3 sequences derived from the VL having the amino acid sequence of SEQ ID NO: 17. In one aspect, the agent comprises HCDR1. HCDR2 and/or HCDR3 sequences derived from the VH having the amino acid sequence of SEQ ID NO: 16, and LCDR1, LCDR2 and/or LCDR3 sequences derived from the VL having the amino acid sequence of SEQ ID NO: 17. The antibody having the heavy chain of SEQ ID NO: 16 and a light chain of SEQ ID NO: 17 neutralizes the inhibitory activity of NKG2A, and also binds the activating receptors NKG2C, NKGE or NKG2H. The antibody does not compete with HLA-E for binding to NKG2A on the surface of a cell (i.e. it is a non-competitive antagonist of NKG2A).

(SEQ ID NO: 16)
EVQLVESGGGLVKPGGSLKLSCAASGFTFSSYAMSWVRQSPEKRLEWVAE

ISSGGSYTYYPDTVTGRFTISRDNAKNTLYLEISSLRSEDTAMYYCTRHG

DYPRFFDVWGAGTTVTVSS (SEQ ID NO: 17)
QIVLTQSPALMSASPGEKVTMTCSASSSVSYIYWYQQKPRSSPKPWIYLT

SNLASGVPARFSGSGSGTSYSLTISSMEAEDAATYYCQQWSGNPYTFGGG

TKLEIKR

In one aspect, the agent comprises amino acid residues 31-35, 50-60, 62, 64, 66, and 99-108 of the variable-heavy ($V_H$) domain (SEQ ID NO: 16) and amino acid residues 24-33, 49-55, and 88-96 of the variable-light ($V_L$) domain (SEQ ID NO: 17), optionally with one, two, three, four, or more amino acid substitutions.

In one aspect, the agent is a fully human antibody which has been raised against the CD94/NKG2A epitope to which any of the aforementioned antibodies bind.

It will be appreciated that, while the aforementioned antibodies can be used, other antibodies can recognize and be raised against any part of the NKG2A polypeptide so long as the antibody causes the neutralization of the inhibitory activity of NKG2A. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. In one embodiment, the epitope is the epitope specifically recognized by antibody having the heavy chain of any of SEQ ID NOS: 2-6 and the light chain of SEQ ID NO: 7.

In one aspect, the agent competes with humZ270 antibody disclosed in U.S. Pat. No. 8,206,709 (the disclosure of which is incorporated herein by reference) in binding to the extracellular portion of human CD94/NKG2A receptor. In one aspect, the agent competes with humanized Z199 antibody disclosed in U.S. Pat. No. 8,796,427 (the disclosure of which is incorporated herein by reference) in binding to the extracellular portion of human CD94/NKG2A receptor. Competitive binding can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g. after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporate herein by reference.

An anti-NKG2A agent such as an antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment.

In a further embodiment, the formulation further comprises a pharmaceutically acceptable preservative. In a further embodiment, the formulation further comprises an isotonic agent. In a further embodiment, the formulation also comprises a chelating agent. In a further embodiment the formulation further comprises a stabilizer. In a further embodiment, the formulation further comprises a surfactant. For convenience reference is made to Remington: *The Science and Practice of Pharmacy*, 19$^{th}$ edition, 1995.

It is possible that other ingredients may be present in the peptide pharmaceutical formulation. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan® (Rituximab), Herceptin® (Trastuzumab) Xolair® (Omalizumab), Bexxar® (Tositumomab) and Campath® (Alemtuzumab) and similar formulations may be used with the antibodies of the disclosure. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Treatment of HNSCC Described are methods useful in the treatment of a carcinomas, particularly a HNSCC cancer, in particularly a non-resectable carcinoma or HNSCC, which is cetuximab-resistant. Cetuximab, (ERBITUX®) is an anti-EGFR antibody that received regulatory (FDA) approval in 2011 for HNSCC.

The cetuximab-resistant carcinoma may have progressed (e.g., not responded, relapsed, spread to other organs) despite prior treatment with cetuximab (and optionally radiotherapy or other treatments). In some embodiments, an individual whose cancer has progressed may have received prior treatment with cetuximab as single agent. In some embodiments, an individual whose cancer has progressed may have received prior treatment with cetuximab combined with a chemotherapeutic agent (e.g. platinum based therapy) or cetuximab combined with radiotherapy. In some embodiments, in addition to a prior course of therapy with cetuximab (optionally further in combination with radiotherapy, chemotherapy and/or other agents), the individual has received a further prior course of therapy with a platinum-based chemotherapeutic agent, wherein the further prior course of therapy with platinum-based agent is administered prior to the course of therapy with cetuximab.

In one embodiment, the carcinoma is HNSCC. HNSCC is a squamous cell or basaloid tumor that arises in the head or neck region and includes tumors of the nasal cavity, nasopharynx, sinuses, lips, mouth and oral cavity, salivary glands, pharynx, hypopharynx or larynx. The treatments disclosed herewith can be particularly useful for example in the treatment of oropharyngeal tumors, tumors of the larynx, tumors of the oral cavity and tumors of the hypopharynx. Such tumors are routinely identified by practitioners in the field of oncology, such as physicians, medical oncologists, histopathologists and otorhinolaryngologists, and head and neck surgeons. Optionally the HNSCC is a non-metastatic HNSCC.

In any embodiments herein, unless the context indicates otherwise, a head and neck cancer (e.g. HNSCC) can optionally be specified as being locally recurrent, distantly metastatic, and/or considered incurable (and any combination thereof, such as for example locally recurrent, locally recurrent and distantly metastatic, locally recurrent and not distantly metastatic, optionally furthermore in any of the foregoing cases, considered incurable.

In one exemplary aspect, provided is a method of stopping, reversing or reducing progression of HNSCC in a mammalian host (e.g., a human patient) having unresectable HNSCC cancer and whose disease or cancer has progressed despite prior treatment with cetuximab alone or cetuximab combined with chemotherapy or with radiation, the method comprising administering to the patient an anti-NKG2A agent (e.g. an anti-NKG2A antibody), an anti-NKG2A antibody composition, or a related composition (e.g., a nucleic acid encoding an anti-NKG2A antibody), in an amount sufficient to detectably reduce the progression of the HNSCC in the host.

In an another aspect, provided is a method of preventing progression of HNSCC to metastatic cancer in a mammalian host (e.g., a human patient) having unresectable, non-metastatic cancer, optionally further wherein the cancer has progressed despite prior treatment with cetuximab, the method comprising administering to the patient an anti-NKG2A agent.

In any embodiment herein, disease, cancer or HNSCC that has progressed despite prior treatment with cetuximab can be referred to as disease, cancer or HNSCC that is cetuximab-resistant. An individual who has a cancer or HNSCC that has progressed despite prior treatment with cetuximab can be referred to as an individual who is (or whose disease, cancer or HNSCC is) cetuximab-resistant.

In one embodiment, the anti-NKG2A agent is administered in combination with cetuximab. The cancer that is resistant or, for example, has progressed can optionally be characterized as a tumor that is resistant to cetuximab treatment, and not, e.g. a new primary tumor. The cetuximab-resistant tumor can for example appear in the same region and during the course of cetuximab treatment or in a limited period after the end of the cetuximab treatment (e.g., 1, 2 or 3 years, or less, for example 3, 4, 6, 9 months).

In one embodiment, provided are compositions for use in the treatment of disease, e.g. cetuximab resistant cancer. In some embodiment, provided is an agent that neutralizes the inhibitory activity of human NKG2A and/or cetuximab, for use in the treatment of a HNSCC in an individual whose HNSCC cancer is resistant to treatment (e.g. prior treatment) with cetuximab (e.g. cetuximab alone or in combination with another agent such as chemotherapy or radiation therapy). In one embodiment, provided is an agent that neutralizes the inhibitory activity of human NKG2A for use in treating a HNSCC in a human individual having received prior treatment with cetuximab, the treatment comprising administering to the individual an effective amount of each of: (a) an agent, optionally an antibody, that neutralizes the inhibitory activity of human NKG2A, and (b) cetuximab. In one embodiment, the cancer or carcinoma is HNSCC.

In one embodiment, provided is cetuximab, for use in the treatment of a HNSCC in an individual having received a prior treatment (e.g. a first course of treatment with cetuximab), wherein said treatment comprises administering to the individual an effective amount of each of: (a) an agent, optionally an antibody, that neutralizes the inhibitory activity of human NKG2A, and (b) cetuximab (e.g. a second course of treatment with cetuximab). Thus, the individual who has received a first, prior, course of treatment with cetuximab, and whose disease progressed during or after such first course of treatment with cetuximab, can be treated with a second course of treatment with cetuximab, in which cetuximab is used in combination with an agent, optionally an antibody, that neutralizes the inhibitory activity of human NKG2A. The individual who has received a first, prior, course of treatment with cetuximab can thus treated with an effective amount of each of: (a) an agent, optionally an antibody, that neutralizes the inhibitory activity of human NKG2A, and (b) cetuximab (a second course of treatment with cetuximab).

In one aspect, the use of cetuximab and/or agent that neutralizes the inhibitory activity of NKG2A is for causing a decrease in tumor burden, optionally for causing a decrease in the sum of diameters of target cell lesions compared to baseline sum of diameters. In one embodiment, the use of cetuximab and/or agent that neutralizes the inhibitory activity of NKG2A is for delaying the progression of cancer. In one embodiment, the use of cetuximab and/or agent that neutralizes the inhibitory activity of NKG2A is for delaying or preventing cancer metastasis.

Suitable treatment protocols for treating the individual include, for example, administering to the individual an effective amount of an antibody that neutralizes the inhibitory activity of human NKG2A, wherein the method comprises at least one administration cycle in which at least one dose of the anti-NKG2A antibody is administered at a dose of 1-10 mg/kg body weight. In one embodiment, the administration cycle is between 2 weeks and 8 weeks.

In one embodiment, the method comprises at least one administration cycle, wherein the cycle is a period of eight weeks or less, wherein for each of the at least one cycles, two, three or four doses of the anti-NKG2A antibody are administered at a dose of 1-10 mg/kg body weight.

In one embodiment, anti-NKG2A is administered in an amount effective to saturate NKG2A receptors on lymphocytes for at least one week, two weeks, three weeks or four weeks. In certain embodiments, a dose (e.g. each dose) of the anti-NKG2A antibody is administered at about 1, 2, 3, 4, 5, 6, 7, 8, 9 or 10 mg/kg.

In one aspect of any of the embodiments herein, the anti-NKG2A antibody is administered once about every two or four weeks.

Delivering anti-NKG2A antibodies to an individual (either by direct administration or expression from a nucleic acid therein, such as from a pox viral gene transfer vector comprising anti-NKG2A antibody-encoding nucleic acid sequence(s)) and practicing the other methods herein can be used to reduce, treat, prevent, or otherwise ameliorate any suitable aspect of cancer progression (notably HNSCC progression). The methods disclosed herewith can be particularly useful in the reduction and/or amelioration of tumor growth, number of tumor cells, and any parameter or symptom associated therewith (e.g. biomarkers). The methods disclosed herewith can be particularly useful in the prevention of tumor relapse, increase in duration of progression free survival, prevention of metastasis. Methods that reduce, prevent, or otherwise ameliorate such aspects of cancer progression, independently and collectively, are advantageous features.

In another aspect, provided is a method of reducing the risk of cancer progression, reducing the risk of further cancer progression in a cell population that has undergone initiation, and/or providing a therapeutic regimen for reducing cancer progression in a human patient. In a further aspect, provided is a method of increasing the likelihood of survival over a relevant period in a human patient diagnosed with HNSCC. In another aspect, provided is a method for improving the quality of life of a HNSCC patient comprising administering to the patient a composition in an amount effective to improve the quality of life thereof. In a further aspect, methods described herein can be applied to significantly reduce tumor size or tumor burden. In a further aspect, methods described herein can be applied to significantly reduce the number of HNSCC cells in a vertebrate host, such that, for example, the total number of HNSCC cells is reduced. In a related sense, provided is a method for killing (e.g., either directly or indirectly causing death of) HNSCC cells in a vertebrate, such as a human cancer patient.

Generally, cancer progression and responses can be determined by an investigator according to standard tumor response criteria conventions, for example according to "Response Evaluation Criteria in Solid Tumors" (RECIST) v1.1 as detailed by Eisenhauer, E A, et al, New response evaluation criteria in solid tumours: Revised RECIST guideline (version 1.1), Eur J Cancer 2009:45:228-247, the disclosure of which is incorporated by reference herein.

As disclosed herein, the NKG2A-neutralizing agent (e.g., an anti-NKG2A antibody) can used to treat an individual in combination with cetuximab. Consequently, upon progression of HNSCC during or after a prior course of cetuximab (the prior course of cetuximab does not comprise combined treatment with NKG2A-neutralizing agent), an individual (e.g. having unresectable, optionally non-metastatic, cancer) can be treated with the combination of NKG2A-neutralizing agent and cetuximab. The prior course of cetuximab can comprise one or more additional agents or therapies, notably radiotherapy and/or chemotherapy.

In some cases, before the prior course of cetuximab (either as single agent or optionally in combination with radiotherapy and/or chemotherapy), the individual will have received a yet earlier prior course of treatment with a platinum-based chemotherapeutic agent; for example the individual has received a course of treatment with a platinum based agent, followed by treatment with the prior course of cetuximab. In this setting, the individual may have experienced cancer progression despite treatment with a platinum based agent, and then received a subsequent treatment with cetuximab (the prior course of cetuximab) optionally wherein cetuximab is administered in combination with radiation therapy and/or chemotherapeutic agent. If the individual then experiences cancer progression despite treatment with the prior course of cetuximab, the individual can be treated with the combination of NKG2A-neutralizing agent and cetuximab.

The combined administration of NKG2A-neutralizing agent and cetuximab includes simultaneous administration of the compounds in the same or different dosage form, or separate administration of the compounds (e.g., sequential administration). Thus, the NKG2A-neutralizing agent and cetuximab can be specified as being formulated for separate administration and are administered concurrently or sequentially. The treatment can optionally be combined with administration of one or more further therapeutic agents. In one embodiment, the course of treatment with NKG2A-neutralizing agent comprises NKG2A-neutralizing agent and cetuximab, and no other therapeutic (e.g. anti-cancer) agents. In another embodiment, the course of treatment with NKG2A-neutralizing agent comprises NKG2A-neutralizing agent, cetuximab, and one more additional therapeutic (e.g. anti-cancer) agents.

As used herein, adjunctive or combined administration of anti-NKG2A agent and cetuximab includes simultaneous administration of the compounds in the same or different dosage form, or separate administration of the compounds (e.g., sequential administration). Thus, the anti-NKG2A and cetuximab can be simultaneously administered in a single formulation. Alternatively, the anti-NKG2A and cetuximab can be formulated for separate administration and are administered concurrently or sequentially.

In the treatment methods, the anti-NKG2A antibody and cetuximab can be administered separately, together or sequentially, or in a cocktail. In some embodiments, cetuximab is administered prior to the administration of the anti-NKG2A antibody. For example, the anti-NKG2A antibody can be administered approximately 0 to 30 days prior to the administration of cetuximab. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of cetuximab. In some embodiments, an anti-NKG2A antibody is administered concurrently with the administration of cetuximab. In some embodiments, an anti-NKG2A antibody is administered after the administration of cetuximab. For example, an anti-NKG2A antibody can be administered approximately 0 to 30 days after the administration of cetuximab. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of cetuximab.

Suitable treatment protocols for treating a human having HNSCC include, for example, administering to the patient an effective amount of each of an antibody that neutralizes the activity of NKG2A and cetuximab, wherein the method comprises at least one administration cycle in which at least one dose of the anti-NKG2A antibody is administered at a dose of 1-10 mg/kg body weight, (e.g. every two weeks), and at least one dose, optionally at least two doses, of cetuximab is administered, optionally wherein cetuximab is administered at a dose of 250 mg/m² weekly, optionally wherein cetuximab is administered at a dose of 400 mg/m² as an initial dose, followed by at least one dose at 250 mg/m² weekly. In any embodiment herein, each dose of anti-NKG2A antibody can be administered at a fixed dose, e.g. a fixed dose between 100-1000 mg, optionally between 200-1200 mg, for example 750 mg.

In one embodiment, the method comprises at least one period of administration (e.g. an administration cycle), wherein the cycle or period is eight weeks (or less), wherein for each of the at least one period, two, three or four doses of the anti-NKG2A antibody are administered at a dose of 1-10 mg/kg body weight (e.g., a fixed dose between 100-1000 mg, optionally between 200-1200 mg, for example 750 mg). In one embodiment, each cycle further comprises the administration of two, three, four, five, six, seven or eight doses of cetuximab at a dose of 250 mg/m². Optionally, the cycle includes the loading dose of cetuximab; i.e. the first dose in the cycle comprises the administration of one initial dose of cetuximab at a dose of 400 mg/m², and subsequent doses of cetuximab at a dose of 250 mg/m².

The anti-NKG2A antibody can advantageously be administered in an amount that achieves a concentration in circulation that is at least 10, 20, or 30 times higher than the concentration required for substantially full (e.g., 90%, 95%) receptor saturation (e.g., as assessed by titrating anti-NKG2A antibody on NKG2A-expressing cells, for example in PBMC), or optionally in an amount that achieves a concentration in a extravascular tissue (e.g. the tumor tissue or environment) that is at least 10, 20, or 30 times higher than the concentration required for substantially full receptor saturation (e.g., as assessed by titrating anti-NKG2A antibody on NKG2A-expressing cells, for example in PBMC).

NKG2A+ NK cell response can be assessed using a suitable assay of cytotoxic activity of NKG2A-expressing NK cells toward HLA-E expressing target cells. Examples include assays based on markers of NK cell activation, for example CD107 or CD137 expression. Advantageously an amount of anti-NKG2A antibody can be administered so at to achieve and/or maintain a continuous (minimum) tissue concentration of at least 10 µg/ml. For example, the blood concentration to be achieved and/or maintained in order to achieve/maintain 10 µg/ml in a tissue can be between 100-110 µg/ml, 100-120 µg/ml, 100-130 µg/ml, 100-140 µg/ml, 100-150 µg/ml, 100-200 µg/ml, 100-250 µg/ml or 100-300 µg/ml.

Exemplary treatment protocols for an anti-NKG2A antibody such as humZ270 (e.g., monalizumab) used in the Examples herein having an $EC_{100}$ for NKG2A+ NK cell response of 1-10 µg/ml, for example about 10 µg/ml, comprise at least one administration cycle in which at least one dose of the anti-NKG2A antibody is administered at a dose of about 10 mg/kg, optionally 2-10 mg/kg, optionally 4-10 mg/kg, optionally 6-10 mg/kg, optionally 2-6 mg/kg, optionally 2-8 mg/kg, or optionally 2-4 mg/kg body weight, optionally a fixed dose of between 100-1000 mg, optionally between 200-1200 mg, for example 750 mg. Optionally, at least 2, 3, 4, 5, 6, 7 or 8 doses of the anti-NKG2A antibody are administered. In one embodiment, the administration cycle is between 2 weeks and 8 weeks. In one embodiment, the administration cycle is 8 weeks. In one embodiment, the administration cycle is 8 weeks and comprises administering one dose of the anti-NKG2A antibody every two weeks (i.e. a total of four doses).

In one aspect of any of the embodiments herein, the anti-NKG2A antibody is administered once about every two weeks.

Exemplary treatment protocols for use with an anti-NKG2A antibody include for example, administering to the patient an anti-NKG2A antibody two times per month and the amount effective to maintain a continuous blood concentration of anti-NKG2A antibody of at least 40 µg/ml between at least two successive administrations of the anti-NKG2A antibody is between 2-10 mg/kg, optionally 2-6 mg/kg, optionally 2-4 mg/kg, optionally about 4 mg/kg body weight, or optionally a fixed dose in the range of 100-1000 mg, optionally in the range of 200-1200 mg, for example 750 mg. These doses can optionally be administered so as to provide for continued blood concentration of anti-NKG2A antibody of at least 40 µg/ml throughout the treatment cycle. Achieving blood concentration of anti-NKG2A antibody of 40 µg/ml is expected to provide a tissue (e.g., extravascular tissue, tumor environment) concentration of about 4 µg/ml, providing at least the $EC_{50}$ for an antibody such as humanized Z270 (e.g., monalizumab).

Exemplary treatment protocols for use with an anti-NKG2A antibody include for example, administering to the patient an effective amount of an anti-NKG2A antibody, wherein the antibody is administered 2 times per month and the amount effective to maintain a continuous blood concentration of anti-NKG2A antibody of at least 100 µg/ml between at least two successive administrations of the anti-NKG2A antibody is between 4-10 mg/kg, optionally 4-6 mg/kg, optionally 4-8 mg/kg, optionally about 4 mg/kg, optionally about 6 mg/kg, optionally about 8 mg/kg, optionally about 10 mg/kg body weight, or optionally a fixed dose in the range of 100-1000 mg, optionally in the range of 200-1200 mg, for example 750 mg. These doses can optionally be administered so as to provide for continued blood concentration of anti-NKG2A antibody of at least 100 µg/ml throughout the treatment cycle. Achieving blood concentration of anti-NKG2A antibody of 100 µg/ml is expected to provide a tissue (e.g., extravascular, tumor environment) concentration of about 10 µg/ml, in turn corresponding to at least the $EC_{100}$ for an antibody such as a humanized Z270.

A patient having a head and neck cancer that has progressed or failed to respond sufficiently upon or following prior treatment with cetuximab can be treated with an NKG2A-neutralizing agent with our without a prior detection step to assess expression of HLA-E on the surface of tumor cells. Thus, optionally, the treatment methods can comprises a step of detecting a HLA-E nucleic acid or polypeptide in a biological sample of a tumor (e.g. on a tumor cell) from an individual. A determination that a biological sample expresses HLA-E (e.g. expresses HLA-E at a detectable level, expresses HLA-E at least at a predetermined level, expresses HLA-E prominently, expresses HLA-E at a high level, or at a high intensity of staining with an anti-HLA-E antibody, in each case optionally compared to a reference) can be used to designate a patient as having a head and neck cancer that may have a particularly strong benefit from treatment with an agent that neutralizes the activity of NKG2A. In one embodiment, the method comprises determining the level of expression of a HLA-E nucleic acid or polypeptide in a biological sample and comparing the level to a reference level (e.g. a value, strong cell surface staining, etc.) corresponding to an individual that benefits from treatment with an agent that inhibits neutralizes the activity of NKG2A. A determination that a biological sample expresses HLA-E nucleic acid or polypeptide at a level that corresponds and/or is increased to the reference level indicates that the individual has a head and neck cancer that can have a particularly strong benefit from being treated with an agent that inhibits neutralizes the activity of NKG2A. Optionally, detecting a HLA-E polypeptide in a biological sample comprises detecting HLA-E polypeptide expressed on the surface of a malignant HNSCC cell. In one embodiment, a determination that a biological sample prominently expresses HLA-E nucleic acid or polypeptide indicates that the individual has a head and neck cancer that may have a particularly strong benefit from treatment with an agent that neutralizes the activity of NKG2A. "Prominently expressed", when referring to a HLA-E polypeptide, means that the HLA-E polypeptide is expressed in a substantial number of tumor cells taken from a given patient. While the definition of the term "prominently expressed" is not bound by a precise percentage value, in some examples a receptor said to be "prominently expressed" will be present on at least 20%, 30%, 40%, 50%, 60%, 70%, 80%, or more of the HNSCC cells taken from a patient.

Determining whether an individual has head and neck cancer cells that express an HLA-E polypeptide can for example comprise obtaining a biological sample (e.g. by performing a biopsy) from the individual that comprises head and neck cancer cells, bringing said cells into contact with an antibody that binds an HLA-E polypeptide, and detecting whether the cells express HLA-E on their surface. Optionally, determining whether an individual has head and neck cancer cells that express HLA-E comprises conducting an immunohistochemistry assay. Optionally determining whether an individual has head and neck cancer cells that express HLA-E comprises conducting a flow cytometry assay.

A patient having a head and neck cancer, in particular HNSCC, can furthermore be treated with the anti-NKG2A agents with our without a prior detection step to assess whether the patient (or the patient's tumor) is HPV positive. In some embodiment, an individual treated with the methods of the invention is HPV-positive. In some embodiment, an individual treated with the methods of the invention is HPV-negative.

EXAMPLES

Example 1—Case of Response Treatment of HNSCC with Repeated Injections of Monalizumab in Combination with Cetuximab in a Cetuximab-Resistant Patient A Phase 1b/2 Trial of IPH2201 and cetuximab was conducted in patients with human papillomavirus (HPV) (+) and HPV (−) squamous cell carcinoma of the head and neck. Although approved in HNSCC after platinum-based therapy, cetuximab has limited activity in that setting (12% response rate). The clinical trial evaluated the efficacy of treatment of HNSCC using monalizumab in combination with cetuximab. Monalizumab (see WHO Drug Information Vol. 30, No. 1, 2016), also referred to as IPH2201, is a neutralizing anti-NKG2A antibody having the heavy chain amino acid sequence shown in SEQ ID NO: 2 and the light chain amino acid sequence shown in SEQ ID NO: 7.

Inclusion Criteria were as follows:

Age ≥18 years

1. Histologically or cytologically-confirmed, HPV (+) or HPV (−) squamous cell carcinoma of the nasopharynx (WHO Type 1), oropharynx, hypopharynx, larynx (supraglottis, glottis, subglottis) or oral cavity.
2. Recurrent or metastatic disease, documented by imaging (CT scan, MRI, X-ray) and/or physical examination. In phase II, measurable disease as per Response Evaluation Criteria in Solid Tumors [RECIST] 1.1 is mandated. In phase Ib, patients with or without measurable disease are eligible.
3. Progression after platinum-based chemotherapy.
4. For phase Ib only: Pretreated patients, and not amenable to further therapy with curative intent. This part is open to pretreated patients regardless of the number of previous treatment lines.
   For phase II only: Patients who received a maximum of two prior systemic regimens for recurrent and/or metastatic disease and not amenable to further therapy with curative intent.
5. No prior treatment by cetuximab except if given for primary treatment (locally advanced disease) with no progressive disease for at least 4 months following the end of prior cetuximab treatment.
6. Recovery from prior surgery and recovery from adverse events to grade 1 or less (except alopecia) due to prior radiation therapy and any systemic therapy.
7. Eastern Cooperative Oncology Group (ECOG) performance status of 0-1.
8. Life expectancy of ≥3 months.
9. Patients with treated brain metastases are eligible if they are ≥4 weeks from therapy completion (including radiation and/or surgery), are clinically stable at the time of study entry and are not receiving corticosteroid therapy at the time of study entry.
10. Adequate hematologic, immunologic, liver and renal function, defined as
    hemoglobin ≥9.0 g/dL,
    absolute neutrophil count ≥1,500/mm3,
    platelets ≥100,000/mm3,
    total bilirubin ≤1.5×institutional upper normal limit (UNL),
    aspartate aminotransferase (AST) and alanine aminotransferase (ALT) ≤2.5×institutional UNL,
    serum creatinine 51.5×institutional UNL or estimated (Cockcroft-Gault formula) or measured creatinine clearance ≥50 mL/min.

11. Negative serum pregnancy test within 72 hours before starting study treatment for women of childbearing potential. Women of childbearing potential and all men must agree to use adequate contraception (hormonal or barrier method of birth control; abstinence) prior to study entry, for the duration of monalizumab administration and for up to 5 months after the last dose of monalizumab.
12. Ability to understand a written informed consent document.
13. Signed informed consent prior to any protocol-specific procedures.

Exclusion Criteria were as follows:
1. For phase II only: Patients who received more than 2 prior systemic regimens for recurrent and/or metastatic disease (no restriction in the phase Ib part of the trial).
2. For phase II only: Patients who received cetuximab or another inhibitor of epidermal growth factor receptor are excluded from the phase II of the trial, except if cetuximab was given as part of a primary treatment approach, with no progressive disease for at least 4 months following the end of prior cetuximab treatment.
3. History of allergic reactions attributed to compounds of similar chemical or biologic composition to cetuximab.
4. Patients with known untreated and uncontrolled brain metastases are excluded. However, brain-imaging studies are not required for eligibility if the patient has no neurological signs or symptoms.
5. Serious concurrent uncontrolled medical disorder.
6. Auto-immune disease, which:
    1. currently or previously required systemic immunosuppressive or immunomodulatory therapy (including corticosteroids administered by systemic route) and/or
    2. has a substantial probability to cause an irreversible injury to any tissue and/or
    3. has been diagnosed less than 3 months before study entry and/or
    4. is clinically unstable and/or
    5. has a substantial risk to progress and cause severe complications.
7. Abnormal cardiac status with any of the following:
    1. Unstable angina
    2. Arrhythmia requiring treatment which is not stabilized by the treatment
    3. QTc>450 ms (M) or 470 ms (F) (Bazett formula –QT Interval/·(RR interval) where RR Interval=60/HR).
8. History of cardiac dysfunction including any of the following:
    1. Myocardial infarction within the last 6 months
    2. History of documented congestive heart failure (New York Heart Association functional classification III-IV).
9. Known interstitial lung disease.
10. Pregnant women are excluded from this study; breastfeeding must be discontinued.
11. Other active invasive malignancy (except for treated basal or squamous cell skin carcinoma, or in situ cervix carcinoma).
12. Treatment with other investigational agents less than 14 days prior to study entry.
13. Systemic treatment with steroids or other immunosuppressive agents within 30 days prior to entry. Physiological replacement with hydrocortisone or equivalent is acceptable.
14. Current active infectious disease.
15. Positive serology for HIV.
16. Positive HBs Ag or positive HBV viremia, Positive HCV viremia.
17. Psychological, familial, sociological, or geographical conditions that do not permit medical follow-up and compliance with study protocol.

The trial included a dose escalation part in which patients received increasing dose levels of 0.4, 1, 2, 4 or 10 mg/kg monalizumab every two weeks, in combination with fixed doses of cetuximab (400 mg/m2 loading dose and then 250 mg/m2 weekly) using a 3+3 design. The cohort expansion part used monalizumab at the highest dose tested 10 mg/kg and included a futility analysis after the first 11 patients. Response rate was evaluated according to RECIST, assessed every 8 weeks. Patients were treated until cancer progression or unacceptable toxicity. The trial remains ongoing in order to enroll further patients and to evaluate duration of response, progression-free and overall survival.

Among the initial partial responses observed was a patient having a history of squamous cell carcinoma of the right lower alveolar ridge, stage T4aN2bM0/IVA, treated with surgical resection with right posterior lateral mandibulectomy with fibular free flap reconstruction, followed by adjuvant radiation. The patient had recurrent squamous cell carcinoma of the oral cavity (not a new primary cancer), p16-negative, which was unresectable. The patient had been previously treated with 3 cycles of cisplatin-taxotere-5 FU (TPF) induction (substituting carboplatin for cisplatin) followed by concurrent chemoradiation with weekly cetuximab. At about 4 months of completion of cetuximab, the patient's PET/CT showed recurrent cancer. The patient was deemed resistant to cetuximab as recurrence was observed slightly more than 4 months after completion of a course of cetuximab plus definitive radiation therapy, the recurrent oral cavity cancer appeared within three years (and thus was not deemed to be a new primary cancer) and was in the same region, in this instance all on the right side. The patient was recommended for the Phase 1b/2 Trial of IPH2201 and cetuximab. Treatment with monalizumab and cetuximab according to the protocol resulted in an objective response (PR), with a best response of a 50% decrease in in target lesions under treatment compared to baseline (before treatment). The measure of lesions is the sum of the longest diameters, or shortest axes if lymph nodes.

Also among the initial partial response observed was a patient with squamous cell carcinoma of the oropharynx, right side laterality, stage TxN2bM0/IVA. The patent's previous courses of treatment included chemotherapy (cisplatin/docetaxel/5FU) during the initial disease stage, followed by radiotherapy. Upon progressive disease the patient was treated for recurrent/metastatic disease with surgery at the initial site and lymph nodes, followed by chemotherapy (cisplatin/carboplatin/5FU), followed by cetuximab. The patient showed progressive disease (as best response) upon cetuximab treatment, and the patient was then treated with paclitaxel and carboplatin. Upon disease progression the patient was included in the Phase 1b/2 Trial of IPH2201 and cetuximab. Treatment with monalizumab and cetuximab according to the protocol resulted in a response (PR).

The finding that neutralizing anti-NKG2A antibody in combination with cetuximab can provide significant amelioration in HNSCC patients who have been deemed resistant to cetuximab provides an opportunity for a significant population of patients with HNSCC who have unresectable cancer and whose cancer progresses despite treatment with cetuximab, particularly in combination with radiotherapy. The treatment may be valuable in preventing further progression, notably to delay or prevent metastatic cancer.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +/−10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of treating a cancer in a human individual having an unresectable HNSCC comprising administering to the individual an effective amount of each of: (a) an agent that neutralizes the inhibitory activity of human NKG2A, and (b) cetuximab, wherein the individual has HNSCC cancer that has progressed despite prior treatment with cetuximab combined with radiotherapy.

2. The method of claim 1, said method comprising:
   a) determining whether an individual has a HNSCC that is resistant to cetuximab as single agent or in combination with radiotherapy and/or a chemotherapeutic agent, and
   b) upon the determination that the individual has HNSCC that is resistant to cetuximab, administering to the individual: (i) the agent that neutralizes the inhibitory activity of human NKG2A, and (ii) cetuximab.

3. The method of claim 1, said method comprising:
   a) determining whether an individual has a HNSCC that comprises malignant cells expressing HLA-E polypeptide, and
   b) upon the determination that the malignant cells express HLA-E polypeptide, administering to the individual: (i) the agent that neutralizes the inhibitory activity of human NKG2A, and (ii) cetuximab.

4. The method of claim 3, wherein determining whether HLA-E polypeptide is expressed by malignant cells comprises obtaining from the individual a biological sample that comprises HNSCC cells, bringing said cells into contact with an antibody that binds a HLA-E polypeptide, and detecting cells that express HLA-E.

5. The method of claim 1, wherein the agent that neutralizes the inhibitory activity of human NKG2A is an anti-NKG2A antibody.

6. The method of claim 5, wherein the anti-NKG2A antibody comprises a human IgG4 constant region.

7. The method of claim 5, wherein the anti-NKG2A antibody comprises the CDR1, CDR2 and CDR3 domains of a heavy chain having the sequence set forth in SEQ ID NO: 2, and the CDR1, CDR2 and CDR3 domains of a light chain having the sequence set forth in SEQ ID NO: 7.

8. The method of claim 5, wherein the anti-NKG2A antibody is administered as a pharmaceutically acceptable composition comprising a therapeutically effective amount of the anti-NKG2A antibody.

9. The method of claim 5, wherein the composition is free of any other pharmaceutically active agents.

10. The method of claim 5, wherein the anti-NKG2A antibody is administered several times at a dosing frequency from once about every week to once about every month.

11. The method of claim 5, wherein cetuximab is administered weekly.

12. The method of claim 1, wherein the treatment comprises at least one administration cycle, wherein the agent that neutralizes the inhibitory activity of human NKG2A is administered every two weeks and cetuximab is administered weekly.

13. The method of claim 1, wherein the treatment comprises at least one period of two weeks, wherein for each of the at least one period, the antibody that neutralizes the inhibitory activity of human NKG2A is administered at a dose of 1-10 mg/kg body weight, and cetuximab is administered in an initial dose of 400 mg/m², and subsequently weekly at 250 mg/m².

14. The method of claim 1, wherein the treatment comprises at least one period of two weeks, wherein for each of the at least one period, the antibody that neutralizes the inhibitory activity of human NKG2A is administered at a fixed dose between 100-1000 mg, optionally 750 mg, and cetuximab is administered in an initial dose of 400 mg/m$^2$, and subsequently weekly at 250 mg/m$^2$.

\* \* \* \* \*

UNITED STATES PATENT AND TRADEMARK OFFICE
CERTIFICATE OF CORRECTION

PATENT NO. : 11,795,222 B2
APPLICATION NO. : 16/979323
DATED : October 24, 2023
INVENTOR(S) : Agnes Boyer-Chammard, Pierre Dodion and Roger Cohen Page 1 of 1

It is certified that error appears in the above-identified patent and that said Letters Patent is hereby corrected as shown below:

In the Specification

Column 17,
Line 33, "region sunderlined)" should read --regions underlined)--.

Column 30,
Line 65, "creatinine 51.5×institutional" should read --creatinine ≤ 1.5×institutional--.

Column 31,
Line 47, "Interval/·(RR" should read --Interval/√(RR--.

Signed and Sealed this
Twelfth Day of March, 2024

*Katherine Kelly Vidal*

Katherine Kelly Vidal
*Director of the United States Patent and Trademark Office*